United States Patent [19]

Lindholm

[11] Patent Number: 4,739,055

[45] Date of Patent: Apr. 19, 1988

[54] ANHYDROUS, STABLE, CRYSTALLINE δ-FORM OF PRAZOSIN HYDROCHLORIDE

[75] Inventor: Stig O. E. Lindholm, Helsinki, Finland

[73] Assignee: Orion-yhtymä Oy, Helsinki, Finland

[21] Appl. No.: 660,871

[22] Filed: Oct. 15, 1984

[30] Foreign Application Priority Data

Jun. 25, 1984 [FI] Finland ................................. 842544

[51] Int. Cl.$^4$ ........................................... C07D 405/14
[52] U.S. Cl. ................................................... 544/291
[58] Field of Search .................... 544/291; 203/14, 67, 203/69

[56] References Cited

U.S. PATENT DOCUMENTS

| | | | |
|---|---|---|---|
| 2,194,851 | 3/1940 | Guinot | 203/14 |
| 2,969,375 | 1/1961 | Ney, Jr. | 203/14 |
| 3,421,983 | 1/1969 | Buchsbaum | 203/14 |
| 3,433,788 | 3/1969 | Somekh et al. | 203/14 |
| 3,511,836 | 5/1970 | Hess | 544/291 |
| 3,738,915 | 6/1973 | Di Fiore et al. | 203/14 |
| 3,743,672 | 7/1973 | Kollar | 203/14 |
| 3,857,759 | 12/1974 | Fiore et al. | 203/14 |
| 3,935,213 | 1/1976 | Hess | 544/291 |
| 4,001,237 | 1/1977 | Partyka et al. | 544/291 |
| 4,026,894 | 5/1977 | Winn et al. | 544/291 |
| 4,092,315 | 5/1978 | Bianco | 544/291 |
| 4,271,300 | 6/1981 | Honkamen et al. | 544/291 |

FOREIGN PATENT DOCUMENTS 156532 9/1982 Fed. Rep. of Germany .

OTHER PUBLICATIONS

Perry, *Chemical Engineers' Handbook*, 4th Ed., McGraw-Hill, New York, pp. 13–49 to 13–51.

Primary Examiner—Glennon H. Hollrah
Assistant Examiner—James H. Turnipseed
Attorney, Agent, or Firm—Burns, Doane, Swecker & Mathis

[57] ABSTRACT

Figure 1:
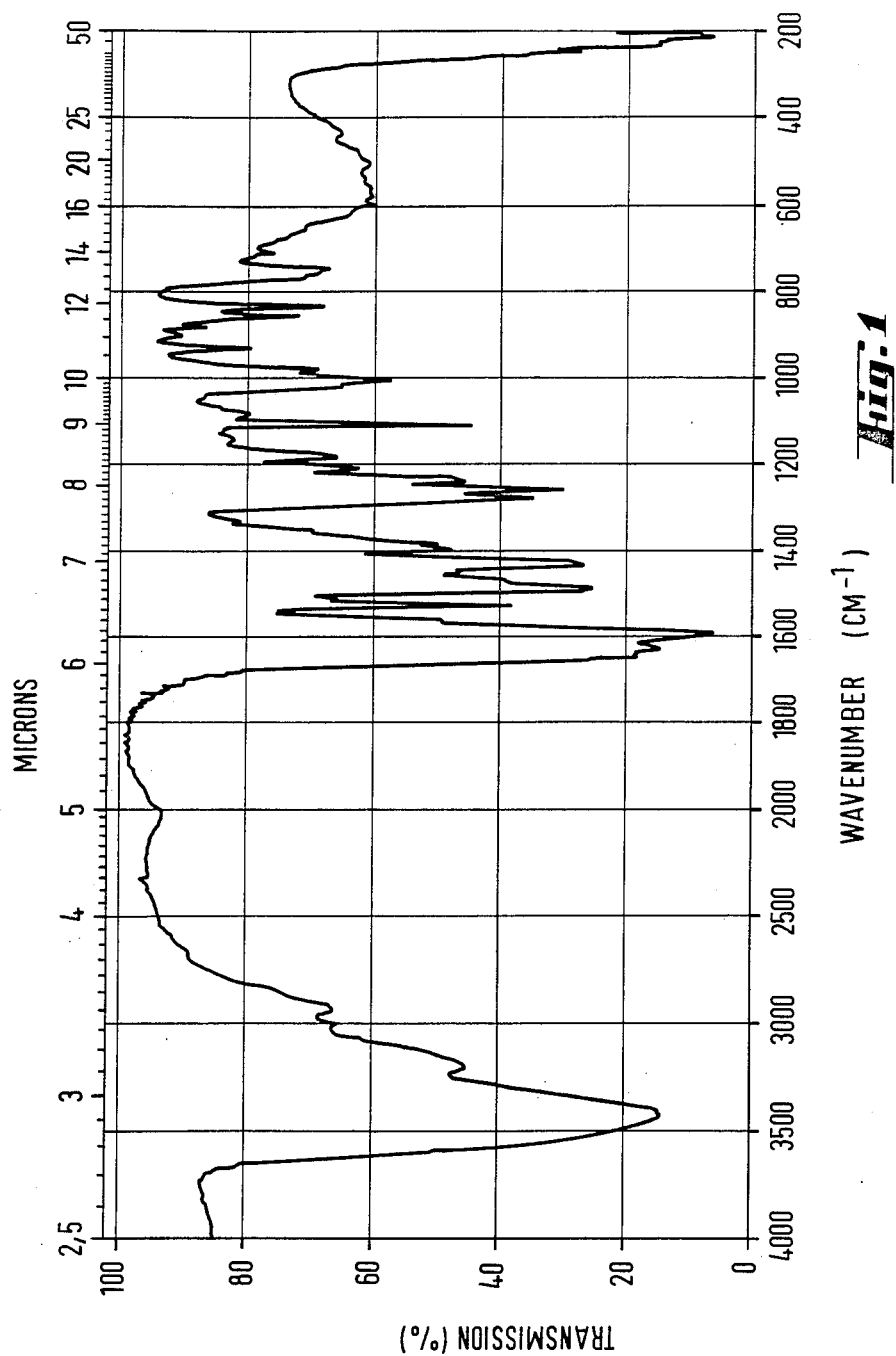
Figure 2:
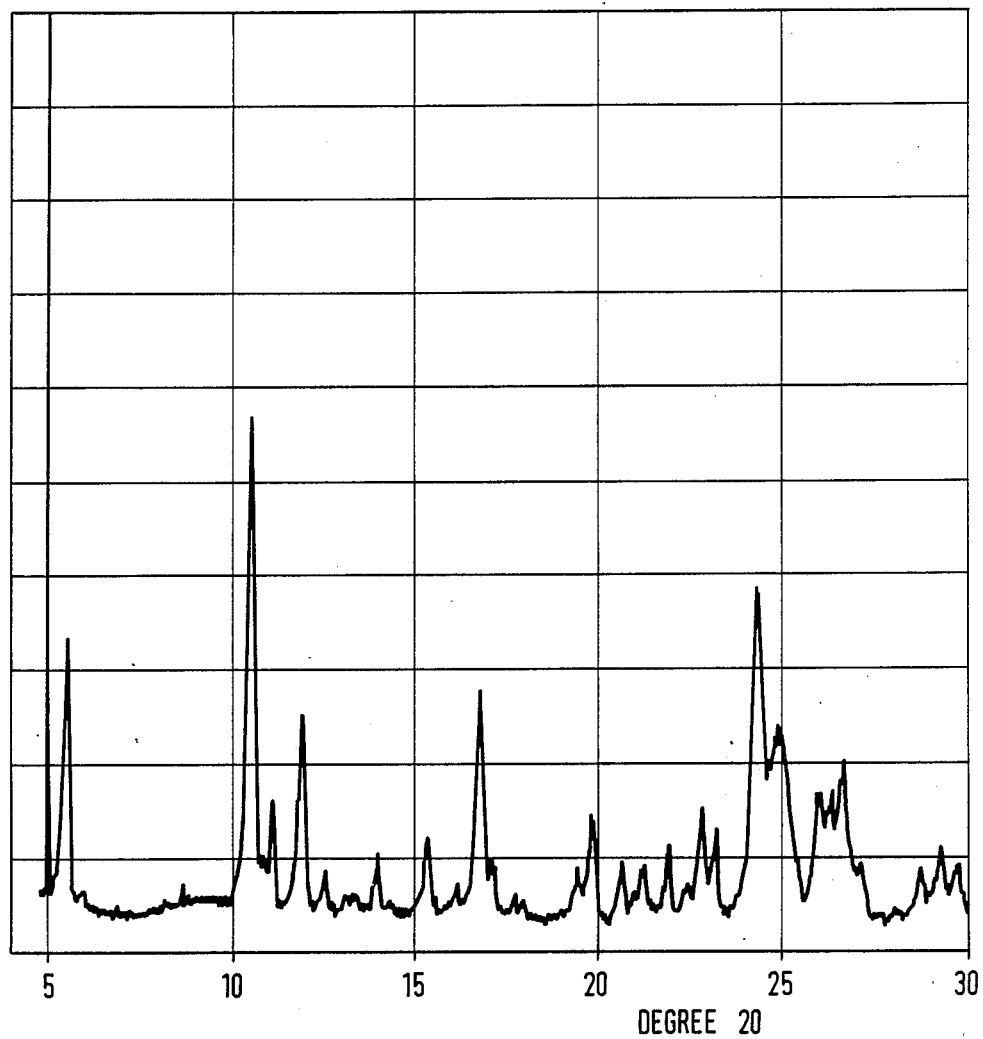

Anhydrous, stable, crystalline δ-form of prazosin hydrochloride, having an infrared spectrum in potassium bromide of FIG. 1 having the following sharp absorption bands at 7.95μ, 13.3μ and a triplet at 9.95μ and the x-ray diffractogram of FIG. 2 having sharp bands in 10.5°, 12.0°, 16.9° and doublets in 24.5° and 26.5°. The δ-form of prazosin hydrochloride is prepared by removing the water of crystallization of prazosin hydrochloride hydrate by azeotropic distillation with selected organic solvents having a boiling point in the range of 55°–160° C. The δ-form of prazosin hydrochloride is useful as a hypotensive agent.

1 Claim, 2 Drawing Sheets

ANHYDROUS, STABLE, CRYSTALLINE δ-FORM OF PRAZOSIN HYDROCHLORIDE

A novel anhydrous, stable, crystalline δ-form of prazosin hydrochloride and a novel process for the preparation of said crystalline δ-form.

The invention is related to a novel, anhydrous, stable, crystalline δ-form of prazosin hydrochloride or 2-[4-(2-furoyl)-piperazin-1-yl]4-amino-6,7-dimethoxyquinazoline hydrochloride. The δ-form is prepared by azeotropic distillation by aid of selected organic solvents.

Prazosin hydrochloride is a well-known hypotensive agent of the following formula:

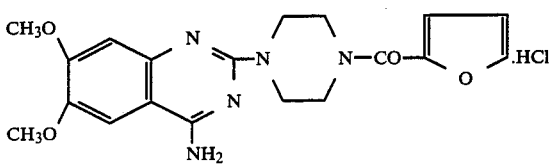

This compound has been disclosed in e.g. U.S. Pat. No. 3,511,836 (DE No. 1,620,138). U.S. Pat. No. 4,092,315 (DE No. 2,708,192) discloses anhydrous, crystalline forms of prazosin hydrochloride, such as the α-, β- and γ-form as well as the amorphous anhydrate.

According to the U.S. Pat. No. 4,092,315 (DE No. 2,708,192) the α-form is relatively non-hygroscopic and stable. Hence it is more advantageous for handling, storing and formulations than the other forms of prazosin hydrochloride.

The term "relatively non-hygroscopic" as used in U.S. Pat. No. 4,092,315 (DE No. 2,708,192) means that a sample initially containing not more that about 0.5% water, when exposed to a temperature of about 37° C. and a relative humidity of about 75% for a period of about 30 days, contains not more than 1.5% water.

U.S. Pat. No. 4,092,315 (DE No. 2,708,192) discloses a process for preparing an amorphous anhydrate of prazosin hydrochloride. The anhydrate is prepared by drying a sample of prazosin hydrochloride polyhydrate in a vacuum desiccator at 100° C. for 12-15 hours. The anhydrate thus prepared is amorphous containing about 1% of water. When samples of the anhydrate are stored at room temperature and 75% relative humidity they absorb moisture rapidly to form the dihydrate (8% water) in about 24 hours. The dihydrate continues to absorb water at a slower rate until an equilibrium water content of 13.5% is obtained after 4 days. Thus the anhydrate is unstable and hygroscopic.

The patent publication DD No. 156,532 discloses a process for preparing the α-form of prazosin hydrochloride by azeotropic distillation of prazosin hydrochloride hydrate in dichlormethane.

Surprisingly we have found that by using selected organic solvents, the boiling point of which are higher than the boiling point of e.g. dichlormethane (b.p. 42° C.), we obtain by aid of azeotropic distillation the anhydrous, stable, crystalline δ-form of prazosin hydrochloride. The infrared spectrum and the X-ray diffractogram of the anhydrous, stable, crystalline δ-form of prazosin hydrochloride are disclosed in FIGS. 1 and 2. The infrared spectrum of the δ-form has the following characteristic absorption bands disclosed in table 1.

TABLE 1

| cm$^{-1}$ | Characteristic bands μ | comments |
|---|---|---|
| 1260 | 7,95 | sharp |
| 755 | 13,3 | |
| 1005 | 9,95 | triplet |

The X-ray diffractogram of the δ-form is characterized by sharp bands at 10.5°, 12.0°, 16.9° and doublets at 24.5° and 26.5°.

The characteristic bands of the infrared spectrum and the X-ray diffractogram do not differ significantly from the respective characteristic bands of the amorphous anhydrate disclosed in U.S. Pat. No. 4,092,315 (DE No. 2,708,192). However the δ-form produced by the process of our invention is stable and crystalline, while the anhydrate disclosed in U.S. Pat. No. 4,092,315 (DE No. 2,708,192) is amorphous, unstable and hygroscopic.

The anhydrous, stable and crystalline δ-form of prazosin hydrochloride is produced by removing the water of crystallization from the dihydrate or polyhydrate prazosin hydrochloride by azeotropic distillation in the presence of selected organic solvents the boiling points of which are in the range of 55°-160° C. Preferred selected organic solvents have a boiling point in the range of 70°-110° C. Examples of such selected organic solvents are hexane (b.p. 69° C.), heptane (b.p. 98° C.) and corresponding alkanes with linear or branched chains or cycloalkanes with a higher boiling point. Benzene (b.p. 78° C.), toluene (b.p. 108° C.), xylenes (b.ps about 137° C.) as well as other aromatic hydrocarbons having a higher boiling point are useful for the preparation of the δ-form. In the process of our invention chloroform (b.p. 60° C.), trichlorethylene (b.p. 86° C.), 1,1-dichlorethane (b.p. 58° C.). 1,1,1-trichlorethane (b.p. 72° C.) and corresponding halogenated hydrocarbons having a higher boiling point can be used.

The δ-form of the prazosin hydrochloride produced by the process of out invention is relatively non-hygroscopic according to the definition of this term in U.S. Pat. No. 4,092,315 (DE No. 2,708,192). In the tests performed the moisture content of the δ-form was within the ranges defined for the term "relatively non-hydroscopic" when the δ-form was stored for 30 days in a temperature of 37° C. and a 75% relative humidity.

The stability of the δ-form of prazosin hydrochloride produced by the process of our invention is also good. Samples were stored for 3 months at 60° C. and the infrared spectra of the samples were compared with the original infrared spectra. No changes cound be found. Samples were also stored at 80° C. and 100° C. without evident changes. The samples were analysed visually and with high pressure liquid chromatography. No visual changes could be observed when the sample was stored for 1 month in daylight.

The process of our invention is advantageous because of the stable product obtained. The solvents used are cheap and easily regenerated. No impurities are produced in the process.

The following examples illustrate the invention.

EXAMPLE 1

1,1,1-trichlorethane (b.p. 72° C.) 100 g of the dihydrate of prazosin hydrochloride prepared according to the process described in pat. No. DE 3,002,553 was suspended in 1000 ml of 1,1,1-trichlorethane. A water separator was connected to the reaction vessel and the mixture was heated with reflux until water no longer separated (1–2 hours). The precipitate was isolated by filtration and the 1,1,1-trichlorethane was evaporated in reduced pressure. The yield was 93 g (100% of the theorethical) δ-form of prazosin hydrochloride, the infrared spectrum and X-ray diffractogram of which was identical with those disclosed in FIGS. 1 and 2.

EXAMPLE 2

Toluene (b.p. 108° C.) 64 g of undried and washed prazosin hydrochloride taken directly from a watercontaining medium (contains 55% water) was suspended in 750 ml toluene and the mixture was heated under reflux as described in example 1. The yield was 19 g (100% of the theoretical) the δ-form of prazosin hydrochloride. The infrared spectrum was identical with the infrared spectrum described in example 1.

EXAMPLE 3

Hexane (b.p. 69° C.) 20 g of the monohydrate of prazosin hydrochloride was suspended in 200 ml of hexane and heated under reflux as described in example 1. The yield was 19 g (100% of the theoretical).

EXAMPLE 4

Heptane (b.p. 98° C.) 20 g of the monohydrate of prazosin hydrochloride was suspended in 200 ml of heptane and heated under reflux as described in example 1. The yield was 19 g (100% of the theoretical).

EXAMPLE 5

Chloroform (b.p. 60° C.) 100 g of the dihydrate of prazosin hydrochloride was suspended in 1000 ml of chloroform and heated under reflux as described in example 1. The yield was 84 g (89% of the theoretical).

EXAMPLE 6

1,2-dichlorethane (b.p. 84° C.). 100 g dihydrate of prazosin hydrochloride was suspended in 1000 ml of 1,2-dichlorethane and the mixture heated under reflux as described in example 1. The yield was 91.5 g (97% of the theoretical).

EXAMPLE 7

Trichlorethylene (b.p. 86° C.) 100 g dihydrate of prazosin hydrochloride was suspended in 1000 ml of trichlorethylene and the mixture was heated under reflux as described in example 1. The yield was 90.5 g (96% of the theoretical).

I claim:

1. Anhydrous, stable, crystalline δ-form of prazosin hydrochloride, having an infrared spectrum in potassium bromide having the following sharp absorption bands at 7.95 u, 13.3 u and a triplet at 9.95 u and the X-ray diffractogram having sharp bands in 10.5°, 12.0°, 16.9° and doublets in 24.5° and 26.5°.

* * * * *